US00PP11961P2

(12) United States Plant Patent
van Veen

(10) Patent No.: US PP11,961 P2
(45) Date of Patent: Jun. 26, 2001

(54) ASTILBE PLANT NAMED 'WHITE WINGS'

(75) Inventor: Wim van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,562

(22) Filed: Dec. 29, 1999

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Astilbe plant named 'White Wings', characterized by its upright and compact plant habit; durable dark green leaves; very freely and uniformly flowering; and attractive white-colored flowers.

2 Drawing Sheets

BACKGROUND OF THE INVENTION

The present invention relates to a new and distinct cultivar of Astilbe plant, botanically known as Astilbe hybrid, and hereinafter referred to by the cultivar name 'White Wings'.

The new cultivar is a product of a planned breeding program conducted by the Inventor in Noorden, The Netherlands. The objective of the breeding program was to develop new compact freely-flowering Astilbe cultivars with attractive flower colors.

The new cultivar originated from a cross made by the Inventor in 1991 of the *Astilbe×Arendsii* cultivar 'Weisse Gloria', not patented, as the male or pollen parent, with the *Astilbe simplicifolia* cultivar 'Hennie Graafland', not patented, as the female or seed parent.

The cultivar 'White Wings' was discovered and selected by the Inventor as a flowering plant within the progeny of the stated cross in a controlled environment in Noorden, The Netherlands.

Asexual propagation of the new cultivar by divisions harvested at Noorden, The Netherlands, has shown that the unique features of this new Astilbe are stable and reproduced true to type in successive generations.

SUMMARY OF THE INVENTION

Plants of the cultivar 'Whate Wings' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'White Wings'. These characteristics in combination distinguish 'White Wings' as a new and distinct cultivar:

1. Upright and compact habit.
2. Durable dark green leaves.
3. Very freely and uniformly flowering.
4. Attractive white-colored flowers.

Plants of the new Astilbe differ from plants of the male parent, the cultivar 'Weisse Gloria', in flower shape, in addition, plants of the new Astilbe are more compact, are more freely flowering, and have whiter flowers than plants of the cultivar 'Weisse Gloria'.

Plants of the new Astilbe differ from plants of the female parent, the cultivar 'Hennie Graafland', in flower color, in addition, plants of the new Astilbe are more freely flowering and have darker green and glossier leaves than plants of the cultivar 'Hennie Graafland'.

BRIEF DESCRIPTION OF THE PHOTOGRAPHS

The accompany colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Astilbe.

The photograph on the first sheet comprises a side perspective view of a typical plant of the new Astilbe.

The photograph at the top of the second sheet comprises a close-up view of typical inflorescences of the new Astilbe.

The photograph at the bottom of the second sheet comprises a close-up view of typical leaves (mature, left, petiole, center; young, right) of the new Astilbe.

DETAILED BOTANICAL DESCRIPTION

In the following description, color references are made to The Royal Horticultural Society Colour Chart except where general terms of ordinary dictionary significance are used. Plants used for the description were about one year-old and grown in 17-cm containers under outdoor production conditions which closely approximate commercial production conditions during the spring and summer in Noorden, The Netherland.

Botanical classification: Astilbe hybrid cultivar 'White Wings'.

Parentage:

*Female parent.*—*Astilbe simplicifolia* cultivar 'Hennie Graafland', not patented.

*Male parent.*—*Astilbe×Arendsii* cultivar 'Weisse Gloria', not patented.

Propagation:

*Type.*—By root divisions.

*Time to rooting.*—About 3 months at temperatures about 18° C.

*Root description.*—Fine.

Plant description:

*Crop time.*—From divisions, about 40 weeks are required to produce fully-grown flowering plants in 17-cm containers.

*Form.*—Upright, compact; inverted triangle.

*Branching habit.*—Flowering stems and leaves arise from the roots.

*Plant height.*—About 40 cm.

*Area of spread.*—About 30 cm.

*Vigor.*—Moderate.

*Stems.*—Length: About 40 cm. Internode length: About 5 cm. Texture: Very sparsely covered with very short (less than 0.5 mm) light brown hairs. Color: 59A to 137A to 139C.

*Foliage description.*—Arrangement: Bi-ternately compound; alternate. Quantity of leaflets per leaf: Typically about 15 to 18. Leaf length, including petiole: About 22 cm. Leaf width: About 14 cm. Leaflet length: About 3.5 cm. Leaflet width: About 1.8 cm. Leaflet shape: Ovate to elliptic. Leaflet apex: Acuminate to acute. Leaflet base: Rounded. Leaflet margin: Doubly serrate, slightly crispate. Leaflet texture: Slightly lustrous; sparsely covered with very short (less than 0.5 mm) light brown hairs along the veins. Leaflet color: Young and mature foliage, upper surface: 137A. Young and mature foliage, lower surface: 137D to 138B. Venation, upper surface: 137A. Venation, lower surface: 183D. Petiole: Length: About 10 cm. Diameter: About 2 mm. Texture: Covered with dark gary-purple chairs, close to 187A, about 1 mm in length. Color: 143A to 187A.

Flower description:

*Flower type and habit.*—Numerous small simgle flowers arranged in branched panicles. Very freely flowering with about 1,300 flowers and flower buds per plant. Flowers sessile.

*Natural flowering season.*—Continuously flowering typically during the early summer.

*Flower longevity.*—Flowers last a few weeks on the plant and more than one week as a cut flower. Flowers persistent.

*Fragrance.*—Faint, not unpleasant.

*Flower buds.*—Length: About 1.5 mm. Diameter: About 0.5 mm. Shape: Ovate to orbicular. Rate of opening: About two to three weeks from visible to fully opened flower. Color: 142D.

*Flower size.*—Length (height): About 3.5 mm. Diameteer: About 2.5 mm.

*Petals.*—Arrangement: Five. Shape: Linear. Apex: Obtuse. Margin: Entire. Length: About 2 mm. Width: About 0.8 mm. Texture: Smooth. Color: When opening, upper and lower surfaces: 142D. Fully opened flower, upper and lower surfaces: 155D.

*Calyx.*—Length: About 3 mm. Width: About 1.5 mm. Number of sepals: About five. Sepal shape: Ovate. Sepal apex: Obtuse. Sepal margin: Entire. Sepal color (Both surfaces): Close to 142D.

*Reproductive organs.*—Stamens: Stamen number: About ten. Anther attachment: Basifixed. Anther length: Less than 0.5 mm. Anther color: Pale creamy white. Pollen amount: Scarce. Pollen color: Pale creamy white. Pistils: Pistil number: Two. Pistil length: About 1.5 mm. Stigma shape: Club-shaped. Stigma color: Creamy white. Style length: About 1.2 mm. Style color: Cream to greenish white. Ovary color: 142C to 142D.

*Seed.*—Length: Less than 0.5 mm. Diameter: Less than 0.5 mm. Color: Light brown.

Disease resistance: Under commercial conditions, plants of the new Astilbe are slightly susceptible to diseases common to Astilbe.

It is claimed:

1. A new and distinct cultivar of Astilbe plant named 'White Wings', as illustrated and described.

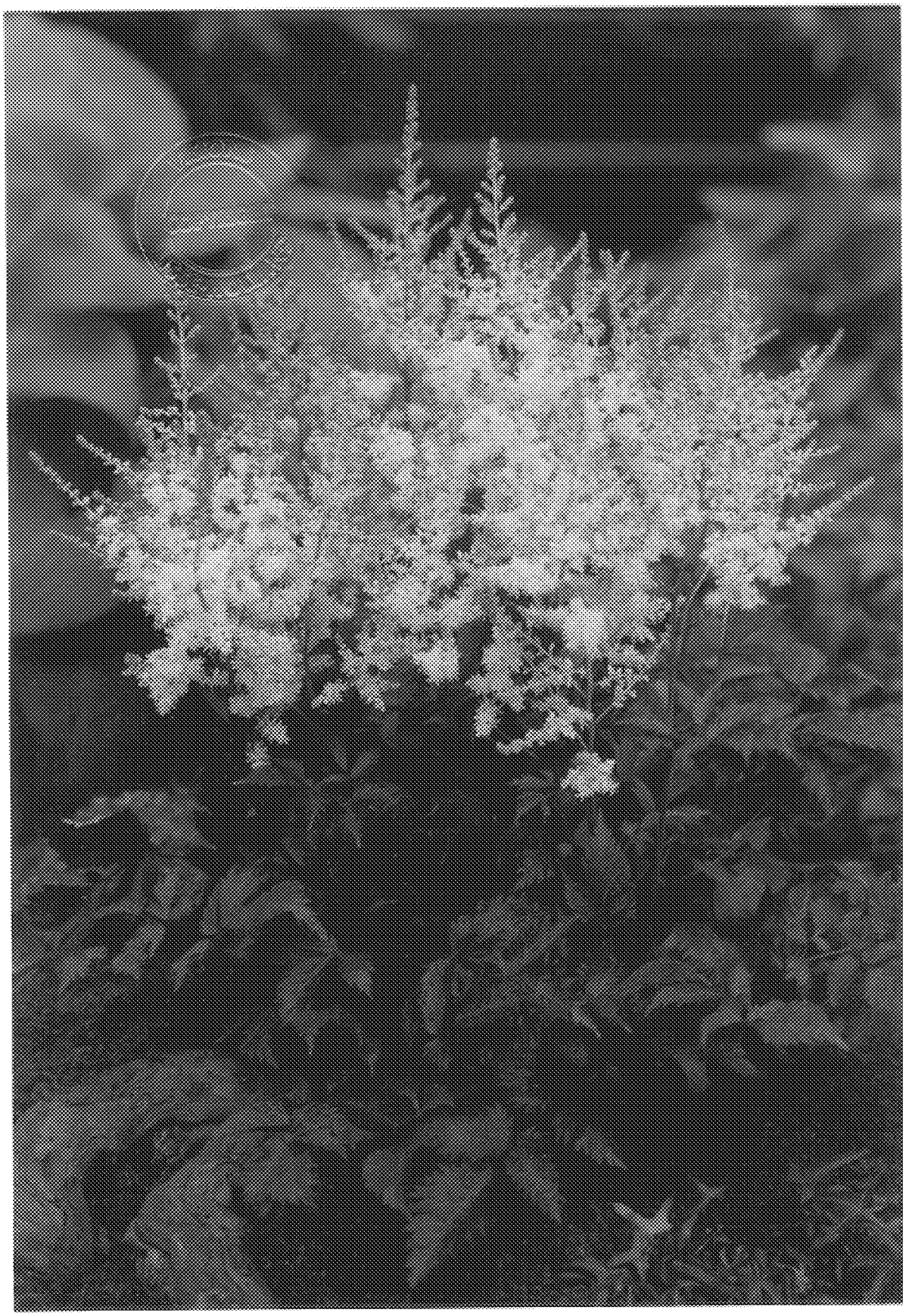

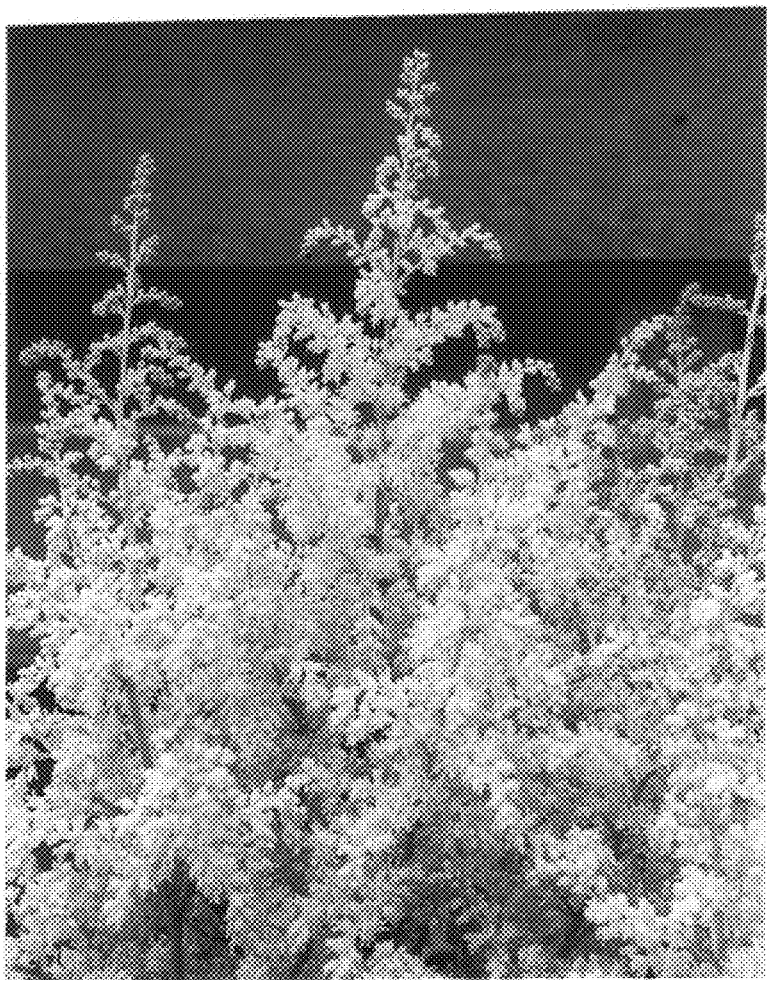
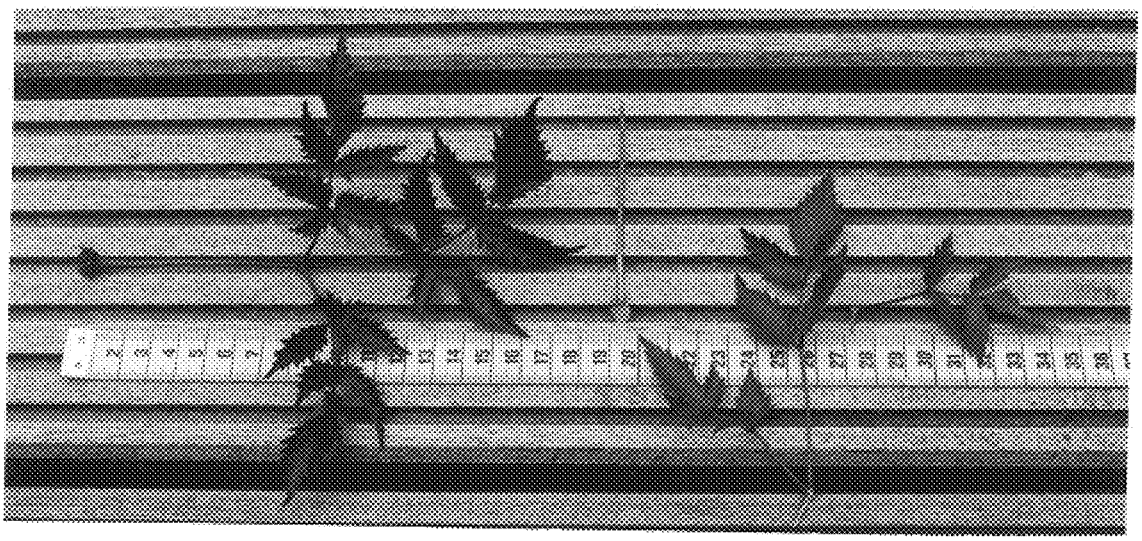

* * * * *